United States Patent
Dunlop et al.

(10) Patent No.: US 6,200,797 B1
(45) Date of Patent: *Mar. 13, 2001

(54) BACTERIAL PROTEIN WITH XYLANASE ACTIVITY

(75) Inventors: Robert William Dunlop, Shenton Park; Bin Wang; Diane Ball, both of Yangebup; Alexander Buhisan Roullo, Forrestfield; Cedric John Falk, Greenwood, all of (AU)

(73) Assignee: Biotech International Limited, Bentley (AU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/817,946

(22) PCT Filed: Oct. 23, 1995

(86) PCT No.: PCT/AU95/00709

§ 371 Date: Oct. 10, 1997

§ 102(e) Date: Oct. 10, 1997

(87) PCT Pub. No.: WO96/13574

PCT Pub. Date: May 9, 1996

(30) Foreign Application Priority Data

Oct. 26, 1994 (AU) .................................. PM9008

(51) Int. Cl.$^7$ ................. C12N 1/20; A21D 2/00
(52) U.S. Cl. ............ 435/252.5; 435/195; 435/200; 435/274; 435/278; 435/839; 426/18; 426/28; 426/53; 426/54; 426/496
(58) Field of Search ................. 435/200, 195, 435/252.5, 839, 278, 274; 426/496, 53, 18, 28, 54

(56) References Cited

U.S. PATENT DOCUMENTS

| | | | |
|---|---|---|---|
| 4,954,447 | * 9/1990 | Nevins et al. ......... | 435/200 |
| 5,306,633 | 4/1994 | Gottschalk et al. . | |

FOREIGN PATENT DOCUMENTS

| | | |
|---|---|---|
| WO 92/03540 | 3/1992 | (WO) . |
| WO 94/04664 | 3/1994 | (WO) . |
| WO 95/27779 | 10/1995 | (WO) . |

OTHER PUBLICATIONS

Fukusaki et al, FEBS Letters 171(2):197–201, 1984.*
Panbangred et al, Agric. Biol. Chem. 47(5):957–963, 1984.*
"Purification and Properties of extracellular Endoxylanases from Alkalophilic thermophilic Bacillus sp.", Dey et al, *Canadian Journal of Microbiology*, vol. 38, No. 5, May 1992, pp. 436–442.
"Thermophilic Alkaline Xylanase from Newly Isolated Alkaliphilic and Thermophilic Bacillus sp. strain", Nakamura et al, *Bioscience biotechnology Biochemistry*, vol. 58, No. 1, Jan. 1994, pp. 78–81.
*Xylans and Xylanases Progress in Biotechnology*, 1992, vol. 7, pp. 325–337, Elsevier Science Publications, ed. J. Visser et al, "Xylanases for the Pulp and Paper Industry", Nissen et al.
*Canadian Journal of Microbiology*, 1993, vol. 39, No. 12, pp. 1162–1166, "Characterization of Cellulase–Free Xylanases from the Newly Isolated Bacillus sp. strain BP–23", (Blanco and Pastor).
*Journal of General Microbiology*, 1993, vol. 139, pp. 1987–1993, "Xylanases from *Streptomyces cyaneus*: Their Production, Purification and Characterization", Wang et al.
*Agric. Biol. Chem.*, 1985, Vol. 49(7), pp. 2033–2039, "Purification and Characterization of Xylanases from Alkalophilic thermophilic Bacillus spp.", Okazaki et al.
Nishitani et al, Plant Physiol. 87:883–890 (1988).*
Bergey's Manual of Systematic Bacteriology, vol. 2, 1986, pp. 1122, 1130.*
Shendye et al, Enzyme Microb. Technol. 15:343–347 (1993).*

* cited by examiner

Primary Examiner—Francisco Prats
(74) Attorney, Agent, or Firm—Larson & Taylor PLC (57) ABSTRACT

The invention relates to specific bacterium and proteins with xylanase activity derived from the bacteria, in particular to xylanases which are free of any significant cellulase activity and which are active at high temperature and at neutral to alkaline pH. Xylanases having these characteristics are particularly useful in the bleaching of wood pulps, such as kraft pulps. The preferred bacterium designated B230 was isolated from white-rotted kerri wood in Western Australia; a sample of which has been deposited under the provision of the Budapest Treaty in the Australian Government Analytical Laboratories under the accession number N94/41262. This preferred bacterium is a gram positive, obligatively aerobic, rod-shaped with a centrally-located spore and has the taxomonic characteristics of *Bacillus subtilis* (by VITEK method).

5 Claims, 4 Drawing Sheets

Figure 3

1. Protein molecular weight marker
2. B230 (HPLC fraction 11) 1638 nkat/ml
3. B230 (HPLC fraction 12) 814 nkat/ml
4. B230 (HPLC fraction 13) 164 nkat/ml

Figure 4

Molecular Weight (daltons)

97,400 –
66,200 –
45,000 –
31,000 –

21,500 –
14,400 –

– Induced xylanase (28 kDa)

1 2 3 4

1   B230 (xylanase induced, concentrated)
2   Protein molecular weight marker
3   B230 (xylanase uninduced)
4   B230 (xylanase induced)

SEQUENCE LISTING

<160> NUMBER OF SEQ ID NOS: 6

<210> SEQ ID NO 1
<211> LENGTH: 17
<212> TYPE: PRT
<213> ORGANISM: Bacillus subtilis

<400> SEQUENCE: 1

```
Ile Thr Lys Asn Gln Thr Gly Asn Arg His Asp Gly Tyr Asp Tyr Glu
 1               5                  10                  15
Leu

<210> SEQ ID NO 2
<211> LENGTH: 22
<212> TYPE: DNA
<213> ORGANISM: Bacillus subtilis
<220> FEATURE:
<223> OTHER INFORMATION: For all n's in this sequence, n=(a or g or c
      or t)

<400> SEQUENCE: 2
aahacnaara aycaracngg na                                              22

<210> SEQ ID NO 3
<211> LENGTH: 22
<212> TYPE: DNA
<213> ORGANISM: Bacillus subtilis

<400> SEQUENCE: 3
ttccactact ttgatatcct tc                                              22

<210> SEQ ID NO 4
<211> LENGTH: 294
<212> TYPE: DNA
<213> ORGANISM: Bacillus subtilis
<220> FEATURE:
<221> NAME/KEY: CDS
<222> LOCATION: (1)..(294)

<400> SEQUENCE: 4 ggg aat acc agt atg acg ctt aat agc ggc ggt gcg ttc agt gcc cag     48
Gly Asn Thr Ser Met Thr Leu Asn Ser Gly Gly Ala Phe Ser Ala Gln
 1               5                  10                  15 tgg agt aac att ggg aat gct tta ttc cga aaa ggc aag aaa ttc gat     96
Trp Ser Asn Ile Gly Asn Ala Leu Phe Arg Lys Gly Lys Lys Phe Asp
             20                  25                  30 tca acg aag act cac tca caa ctt gga aat ata tca atc aat tac aac    144
Ser Thr Lys Thr His Ser Gln Leu Gly Asn Ile Ser Ile Asn Tyr Asn
         35                  40                  45 gca acc ttc aat ccc ggg ggg aat tcc tat ctg tgt gtt tat gga tgg    192
Ala Thr Phe Asn Pro Gly Gly Asn Ser Tyr Leu Cys Val Tyr Gly Trp
     50                  55                  60 acg aaa gat ccg ctc aca gaa tat tac atc gtc gat aat tgg ggc acc    240
Thr Lys Asp Pro Leu Thr Glu Tyr Tyr Ile Val Asp Asn Trp Gly Thr
 65                  70                  75                  80 tac aga ccg acg gga aac gcc gaa ggg tac ttt tac tgt tga tgg ggg    288
Tyr Arg Pro Thr Gly Asn Ala Glu Gly Tyr Phe Tyr Cys     Trp Gly
                 85                  90                  95 cac ata                                                             294
His Ile

<210> SEQ ID NO 5
<211> LENGTH: 93
<212> TYPE: PRT
<213> ORGANISM: Bacillus subtilis

<400> SEQUENCE: 5

Gly Asn Thr Ser Met Thr Leu Asn Ser Gly Gly Ala Phe Ser Ala Gln
 1               5                  10                  15

Trp Ser Asn Ile Gly Asn Ala Leu Phe Arg Lys Gly Lys Lys Phe Asp
```

```
                    20                    25                    30
Ser Thr Lys Thr His Ser Gln Leu Gly Asn Ile Ser Ile Asn Tyr Asn
             35                    40                    45

Ala Thr Phe Asn Pro Gly Gly Asn Ser Tyr Leu Cys Val Tyr Gly Trp
         50                    55                    60

Thr Lys Asp Pro Leu Thr Glu Tyr Tyr Ile Val Asp Asn Trp Gly Thr
 65                    70                    75                    80

Tyr Arg Pro Thr Gly Asn Ala Glu Gly Tyr Phe Tyr Cys
                 85                    90

<210> SEQ ID NO 6
<211> LENGTH: 4
<212> TYPE: PRT
<213> ORGANISM: Bacillus subtilis

<400> SEQUENCE: 6

Trp Gly His Ile
```

BACTERIAL PROTEIN WITH XYLANASE ACTIVITY

This invention relates to proteins with xylanase activity derived from bacteria, and in particular to xylanases which are free of any significant cellulase activity and which are active at high temperature and at neutral to alkaline pH. Xylanases having these characteristics are particularly useful in the bleaching of wood pulps, such as kraft pulps.

BACKGROUND OF THE INVENTION

Enzymes are proteins present in all living cells, where apart from controlling metabolic processes, they break down food materials into simpler compounds. The enzymes are catalysts which speed up processes which would otherwise proceed very slowly, or not at all. Moreover, enzymes are very specific, breaking down only one type of compound.

Xylan is a polysaccharide found in most plant cell walls, consisting of D-xylose units linked by β-1-4 glycosidic bonds. It occurs with another polysaccharide, cellulose and an amorphous binding polymer, lignin. Xylan forms a major component of plant hemicelluloses, and varies in the nature of substituents on the sugar groups, depending on the origin. For example, xylans derived from hardwoods typically consist of a backbone of O-acetyl-4-O-methylglucuronoxylan, in which about 10% of the xylose units carry 4-O-methylglucuronic acid side chains linked via α-1,2 bonds, and 70% of the xylose residues are acetylated at C-2 or C-3. In contrast, xylans derived from softwoods are usually arabino-4-O-methylglucuronoxylans in which over 10% of the xylose sub-units carry arabinofuranose residues linked via α-1,3 bonds. Enzymes which are able to degrade xylan are called xylanases (endo-1,4-β-D-xylanases; International enzyme nomenclature EC 3.2.1.8).

Commercial preparations of xylanase, often in combination with other cell wall degrading enzymes, have been used in the extraction or liquefaction of plant material. For example, in the food industry, the mashing process for the production of juices can be made to produce higher yields and better processing with the application of cell wall degrading enzymes, which include xylanase.

The primary source of cellulose for paper manufacture is wood, and may be either hardwood or softwood. The initial step in paper manufacture is the reduction of wood to the fibre state, which may be achieved by mechanical or chemical pulping methods. Chemical pulping involves the "cooking" of woodchips with chemical reagents in order to separate the cellulose fibres from the other wood components, and to break down the lignin and other extraneous compounds so that the cellulose is left in tact in its fibrous form. The most common process is the kraft or sulphate process, which can be applied to almost any timber species. The active ingredients are sodium hydroxide and sodium sulphide in a strongly alkaline solution.

During the kraft pulping process, xylan in the wood is initially dissolved in the pulping liquor, but with time, reprecipitates on to the resulting pulp. Wood lignin is modified and dissolved by the pulping liquors. However, about 10% of the lignin remains in the kraft pulp. To brighten the pulp, the lignin must be removed by bleaching chemicals, such as chlorine, which generate environmentally hazardous wastes.

More recently, commercial xylanase preparations have been used as an aid to the bleaching of kraft wood pulps. A program of cooperation between research institutes and the pulping industry has shown that treating the unbleached kraft pulp with xylanase results in a reduciton in the amount of bleaching chemicals required to obtain a full brightness pulp. It is believed that xylanase acts as a bleaching aid (bleach booster) by releasing some trapped residual lignin within the pulp matrix and giving better access to bleaching chemicals. It is widely believed that xylanase breaks down reprecipitated xylan which forms a coating on the pulp, thus releasing trapped residual lignin from within the pulp matrix, and allowing better access of bleaching chemicals to this matrix. Thus xylanase acts as a bleaching aid or bleach booster.

In the kraft process, the pulp is typically handled at high temperatures and neutral to alkaline pH. Commercial xylanases typically have a temperature optimum of about 50° C. and a pH optimum of about 5, and are thus subject to rapid denaturation under process conditions. Thus there is a need for xylanases which are able to act optimally on the kraft pulp without any requirement to adjust the temperature or pH. In order to be useful as a bleaching aid, the xylanase must also be free of any significant cellulase activity, since cellulase would cause an undesirable loss of cellulose fibre.

We have screened microorganisms newly isolated from a range of environments in order to identify those which produce high levels of xylanases with high temperature optima and which are active at neutral to alkaline pH. A previously unidentified bacterium isolated from white-rotted wood, produces such a xylanase in high yield and free of significant cellulase activity. Thus bacterium is a strain of *Bacillus subtilis* which we have designated B230.

SUMMARY OF THE INVENTION

According to one aspect, the invention provides a bacterium, isolatable from wood compost, having the following characteristics:

A. Ability to grow at a temperature between 20° and 45°;

B. Ability to grow in the pH range of 5 to 9.5;

C. Ability to grow on Luria-Bertani agar at 37°;

D. Ability to grow under solid state or submerged culture conditions; and

E. Constitutive production and/or extracellular release of at least one protein with xyalanse activity having an associated cellulase activity of less than 0.1, said at least one protein having a molecular weight of about 28 kD.

Preferably the bacterium is isolated such that a biologically pure culture exits.

Preferably xylanase production is enhanced by growth in the presence of xylan or of lignocellulose substrates, or degradation products, including xylose and xylitol, derived from such substrates.

More preferably the xylanase has at least one characteristic selected from the group consisting of activity at about pH between 4.5 and 9.5, a thermal activity range up to 70° C., and high thermal stability up to 65° C. Most preferably the xylanase produced by the bacterium is effective on both soluble and insoluble xylans.

In a particularly preferred embodiment, the bacterium has the characteristics of the bacterial isolate designated B230, as deposited under the provisions of the Budapest Treaty in the Australian Government Analytical Laboratories, PO Box 385, Pymble, New South Wales 2073, Australia, on Sep. 6, 1994, under Accession No. N94/41262, or a mutant or derivative thereof having the ability to produce a xylanase as described above. The term "mutant or derivative" thereof includes naturally occurring and artificially induced mutants which retain their ability to digest xylans. Production of such mutants or derivatives will be well known by those skilled in the art.

According to a second aspect, the invention provides a process for producing at least one protein with xylanase activity said process comprising cultivating a bacterium under conditions and for a time sufficient to produce said protein and collecting culture medium wherein said bacterium has the following characteristics:

A. Ability to grow at a temperature between 20 and 45°;

B. Ability to grow in the pH range of 5 to 9.5;

C. Ability to grow on Luria-Berani agar at 37°;

D. Ability to grow under solid state or submerged culture conditions; and

E. Constitutive production and/or extracellular release of at least one protein with xylanase activity, said protein having an associated cellulase activity of <0.1%.

Preferably the bacterium used is strain B230 or a mutant, variant or derivative thereof.

Preferably the bacterium is grown under optimal conditions for extracellular production of said at least one protein. Still more preferably the production of said at least one protein is induced by the addition of xylitol to the culture medium. Preferably xylitol is added in an amount of 0.01 to 2% of the culture medium which is preferably a broth.

According to a third aspect, the invention provides a protein with xylanase activity said protein having an associated cellulase activity of less than 0.1% and a molecular weight of about 28 kD as determined by SDS-PAGE. Preferably the protein has at least one characteristic selected from the group consisting of activity at about pH between 4.5 and 9.5, a thermal activity range up to 70° C. and high thermal stability up to 65° C. Preferably the protein is effective in digesting both soluble and insoluble xylans.

Preferably the protein with xylanase activity is isolatable from the bacterium described above. More preferably the protein is isolated from the bacterial strain B230.

Preferably the protein with xylanase activity is an isolated preparation meaning that it has undergone some purification away from other proteins and/or non-proteinatious material. The purity of the preparation may be represented as at least 40% protein with xylanase activity, preferably at least 60% protein, more preferably at least 75% protein with xylanase activity, still more preferably at least 80% protein with xylanase activity or greater, as determined by weight, activity, amino acid composition or similarity, antibody reactivity or any other convenient means.

According to a fourth aspect, the invention provides a composition comprising said protein with xylanase activity as an active ingredient together with an industrially acceptable stabiliser. The composition may be used as a bleaching aid or bleaching booster or in paper deinking. Those skilled in the art will be familiar with the types of industrially acceptable stabilisers which may be used such as glycerol, sorbitol or other polyalcohols.

The composition described above is for use in bleaching kraft pulp or deinking paper. Accordingly, in a fifth aspect the present invention provides a method of bleaching wood or paper pulp comprising administering a bleaching aid or bleaching booster effective amount of the composition to said pulp, for a time and under conditions sufficient to achieve the desired bleaching of the pulp.

The protein of the present invention may also be used in the preparation of animal feed and in preparation of dough for bread-making.

We have found that the bacterium B230, when grown under suitable fermentation conditions, will produce xylanase which accumulates in the extracellular fermentation broth. The xylanase from such a broth has a thermal activity range from ambient up to 70° C. and a useful pH range from 5 to 9, with optimal activity at pH 6–6.5. The xylanase has very high thermal stability, retaining 100% activity after 3 hrs and 90% activity after 22 hrs at 60° C. Cellulase activity associated with the xylanase is minimal (<0.1%).

The crude preparation may be used however partially purified xylanase may also be used.

While the following description refers to a single xylanase, our results indicate that there are in fact at least two different xylanases produced during fermentation of bacterium B230, and all xylanases produced by this organism are within the scope of the invention.

DESCRIPTION OF THE INVENTION

The invention will now be described by way of reference only to the following non-limiting examples, and to the figures in which:

EXAMPLE 1

A bacterium which we have designated B230 was isolated from a sample of white-rotted karri wood; this sample was collected from near Walpole, Western Australia, in May 1993.

Approximately 0.5 g of sample was placed in a 25 mL conical flask. To this was added 10 mL of sterile deionised water, and the flask was placed on an orbital shaker at room temperature for 30 minutes. Serial dilutions of the water dispersion were prepared as follows:

0.9 mL of sterile water was added into four 1 mL sterile tubes. A sample of water (0.1 mL) from the 10 mL flask was added to the first tube. The contents of the tube were mixed well, and 0.1 mL added to the second tube, and the procedure was repeated down to the fourth tube.

Samples (0.1 mL) from each tube was streaked onto Luria-Bertani agar. The agar plates were sealed and placed in a incubator at 37° C. overnight. Colonies of bacteria appeared on the plates, and individual colonies were picked off and replated onto fresh Luria-Bertani plates.

The composition of Luria-Bertani medium is:

typtone 10 g yeast extract 5 g sodium chloride 10 g deionised water 1L

For Luria-Bertani (LB) agar, 18 g of agar is added to the above components. All media were sterilised by autoclaving at 121° C. for 20 minutes.

The organism was isolated in pure culture, and a sample was deposited under the Budapest Treaty in the Australian Government Analytical Laboratories as described above.

The bacterium has the following taxonomic characteristics:

rod-shaped bacterium with a centrally-located spore
Gram positive
obligately aerobic
*Bacillus subtilis* (by VITEK method)

EXAMPLE 2

Growth Conditions

The bacterium is not fastidious, and can be grown on a range of media, including LB broth. The requirements are:

1. a source of carbon, most conveniently a carbohydrate such as dextrose,
2. a source of nitrogen, most conveniently as a tryptone, and
3. complex nutrients, most conveniently as yeast extract.

The bacterium can be grown within the temperature range 20 to 45° C. and within the pH range 5 to 9.5.

The bacterium can be grown successfully under different fermentation conditions, including solid state or submerged culture; fermentation continues under aerobic conditions with or without agitation.

EXAMPLE 3

Production and Characterisation of Xylanase

When grown under the conditions described in Example 2, bacterium B230 synthesises xylanase, and releases the enzyme into the extracellular medium. While xylanase is produced constitutively, addition of xylan to the culture medium as an additional carbon source further enhances the level of xylanase production. The added xylan may be in the form of isolated wood xylan, or may be a component of lignocellulosic material such as wheat bran.

Xylanase was assayed using the following conditions:

Substrate: 1% birchwood xylan

Buffer: 50 mM sodium phosphate/citric acid, pH 6.

Incubation temperature: 50° C.

Incubation time: 20 minutes

The enzyme reaction was stopped with 3,5-dinitrosalicyclic acid (DNS) reagent which measures, using xylose standards, the amount of reducing sugar produced in 20 minutes. Enzyme units are expressed in nanokatals (nkats), where 1 nkat is the amount of xylanase which will produce 1 nmole of xylose per second under the defined conditions.

EXAMPLE 4

Production of Xylanase by Submerged Fermentation

Xylanase from B230 can conveniently be prepared by submerged fermentation. B230 seed culture can be prepared overnight in LB broth at 37° C. This inoculum is added to an LB broth containing beechwood xylan (2% w/v). The pH of the broth is increased to pH 7.8 by the addition of 2M sodium hydroxide, and the temperature adjusted to 37° C. The broth is stirred (1,000 rpm) and aerated with filtered sterile air (0.7 L of air/L of broth/min).

The seed inoculum is added to the broth and the above conditions of temperature, pH, agitation and aeration maintained. Samples of culture are taken at regular intervals to monitor the production of xylanase. Optimal levels of xylanase (11,000 nkat/mL) are obtained within 90 hours of fermentation.

EXAMPLE 5

Characterisation of Xylanase

The crude enzyme preparation from the fermenter broth was characterised with respect to pH and temperature.

a) pH Optimum

Figure 1:
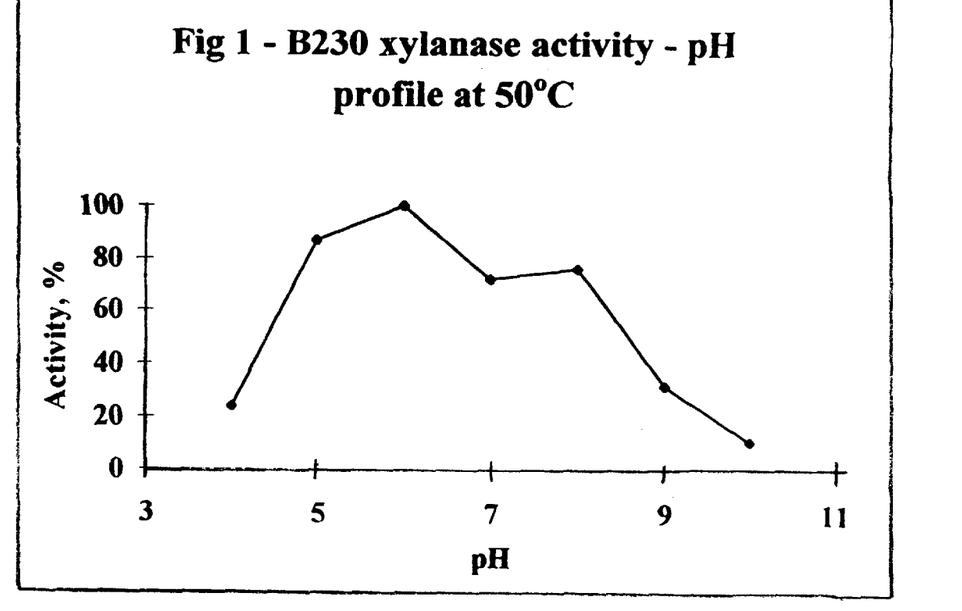
FIG. 1 shows the variation of activity of xylanase from bacterium B230 with pH compared with that from bacterium B698.

The xylanase activity was determined as described above, with the exception that the buffer was changed to obtain a stable pH. The results are listed in Table 1 below. The data is further expressed in FIG. 1. The optimal pH for xylanase activity was found to be pH 6–6.5.

TABLE 1

| pH Profile of B230 Xylanase | |
|---|---|
| pH | Relative Xylanase Activity (%) |
| 4 | 24 |
| 5 | 87 |
| 6 | 100 |
| 7 | 72 |
| 8 | 76 |
| 9 | 32 |
| 10 | 11 | b) Temperature Optimum

Figure 2:
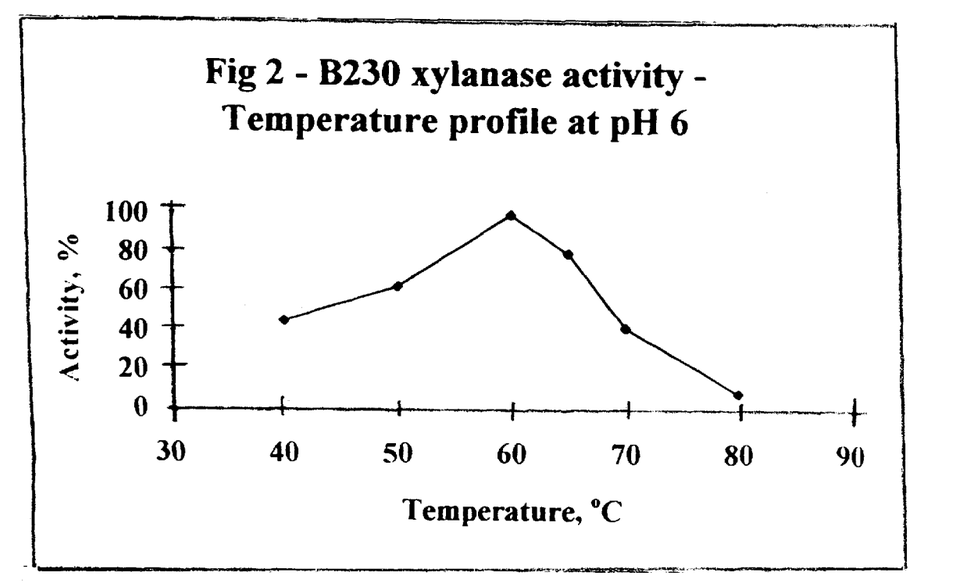
FIG. 2 illustrates the variation in activity of xylanase from bacterium B230 with temperature, compared with that from bacterium B698.

The xylanase activity of B230 enzyme was determined as described above, except that the temperature was altered within the range from 40 to 80° C. Results are listed in Table 2 and further expressed in FIG. 2. The optimal temperature for xylanase activity was found to be 60° C.

TABLE 2

| Temperature Profile of B230 Xylanase | |
|---|---|
| Temperature (° C.) | Relative Xylanase Activity (%) |
| 40 | 45 |
| 50 | 63 |
| 60 | 100 |
| 65 | 80 |
| 70 | 42 |
| 80 | 8 |

EXAMPLE 6

Thermal Stability

The stability of B230 xylanase was determined at pH 6 and 60° C., the optimal pH and temperature respectively for the enzyme system. Samples were tested for residual activity at regular intervals as described in the xylanase assay conditions above. After 3 hours, 100% xylanase activity was retained. Even after 22 hours, 90% of the xylanase activity was retained. Thus, xylanase from B230 is very thermally stable.

The thermal stability at 60° C. and 65° C. at different pH values were determined over 2 hours. Results are in Table 3.

TABLE 3

Thermal Stability 60, 65° C., 2 hrs

| | Relative Xylanase Activity | |
|---|---|---|
| pH | 60° C. | 65° C. |
| 6 | 100 | 71 |
| 7 | 117 | 48 |
| 8 | 84 | 7 |
| 9 | 55 | 0 |

EXAMPLE 7

Stability at 4° C.

The stability of B230 xylanase was determined at 4° C. by storing it at that temperature. Samples were tested for activity at regular intervals under the conditions described in the xylanase assay conditions above. After 22 days, 100% of the original activity was retained.

EXAMPLE 8

Purification of Xylanase

Figure 3:
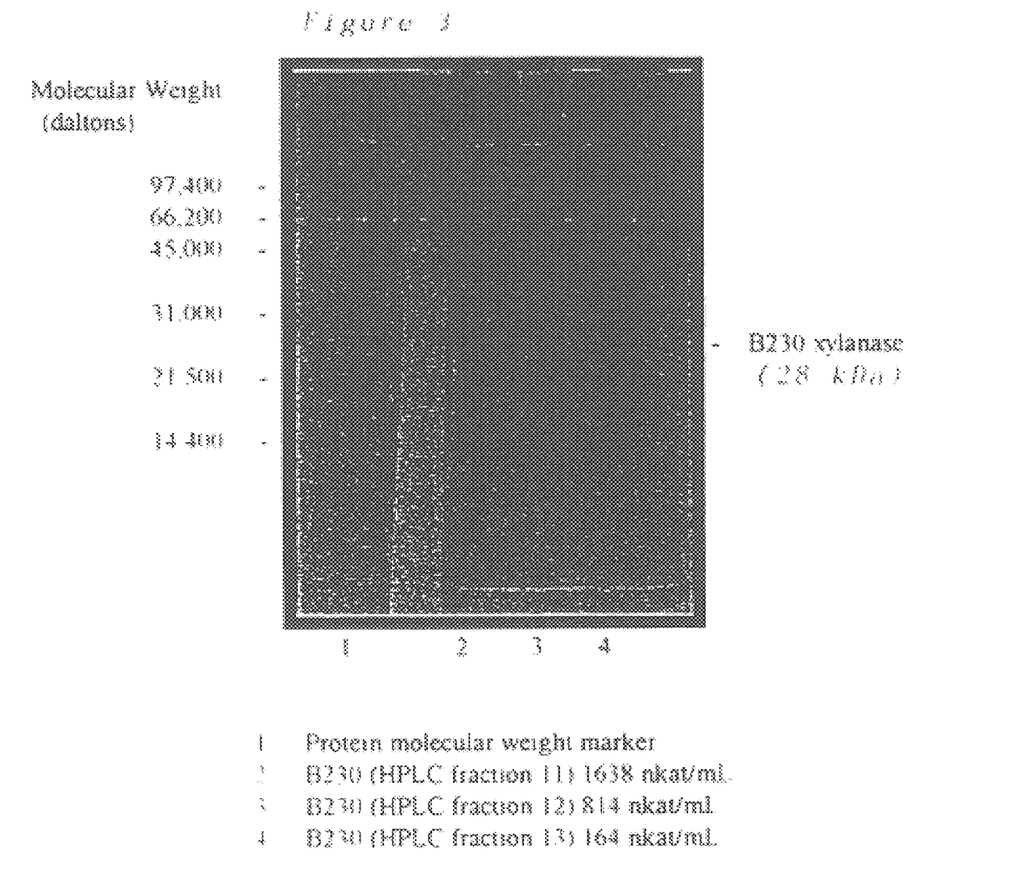
FIG. 3 is a photograph of a SDS-PAGE gel of the purified enzyme having an approximate molecular weight of 28 kD.

A fraction of xylanases was partially purified by conventional purification techniques involving DEAE Sepharose and size exclusion chromatography. The xylanase fraction had a single band on SDS-PAGE at 28 kDa as shown in FIG. 3 and a purity of >80%.

EXAMPLE 9

Induction of 28 kDa Xylanase

Figure 4:
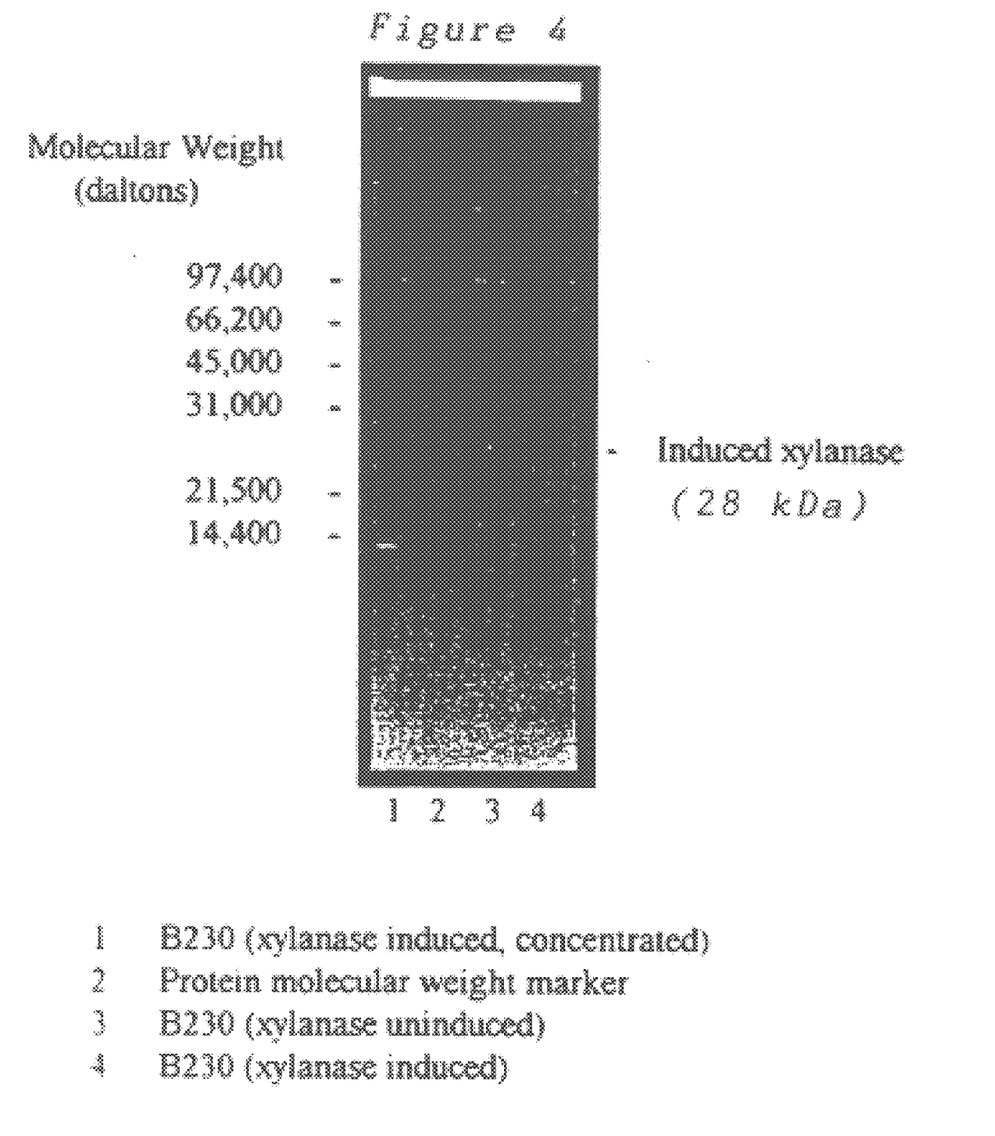
FIG. 4 is a photograph of a SDS-PAGE gel of fermenter broth proteins including xylitol induced xylanase. Compared with proteins from non-induced cultures, the xylanase protein can be identified as having an approximate molecular weight of 28 kD.

B230 seed culture was prepared overnight in LB broth at 37°. This inoculum was added equally to 2 flasks containing corn steep liquor (2%) and incubated at 37° C. To one flask, xylitol (to 0.1%) was added daily for 5 days. After 5 days both flask broths were centrifuged. The cell free broths were assayed for xylanase activity. Xylitol induces xylanase (2,000 nkat/ml) compared with uninduced broth (50 nkat/ml). A sample of each broth was concentrated by ultrafiltration (5 kKa membrane), and the retentate run on an SDS-PAGE gel. As shown in FIG. 4, a protein band at approximately 28 kDa was induced by xylitol. This is consistent with the purified xylanase in Example 8, FIG. 3.

EXAMPLE 10

Use of B230 Xylanase as a Bleaching Aid

The crude xylanase system (167 nkat/g of pulp) was mixed with unbleached kraft pulp (35 g oven dried basis) at consistency 8% and adjusted to pH 5, 7 or 9 with appropriate buffer. The mixture was incubated for 1 hr at 60° C. The pulp was then bleached with chlorine dioxide-sodium hydroxide-chlorine dioxide. The results are shown in Table 4.

TABLE 4

Kraft Pulp Bleaching B230 X at 60° C., 1 hr

| | Bleached pulp | | |
|---|---|---|---|
| Treatment | Brightness (%) | Kappa Number | Yield (%) |
| (pH 5) DED (control) | 78.4 | 2.21 | 98.8 |
| (pH 5) XDED | 79.4 | 2.04 | 98.9 |
| (pH 7) DED (control) | 77.4 | 2.35 | 98.1 |
| (pH 7) XDED | 81.6 | 1.74 | 97.6 |
| (pH 9) DED (control) | 76.8 | 2.45 | 99.4 |
| (pH 9) XDED | 81.4 | 1.75 | 98.7 |

$D_1$—chlorine dioxide, 2.5% as chlorine, 70° C., 2 hr
$D_2$—chlorine dioxide, 0.5% as chlorine, 70° C., 1 hr
E—sodium hydroxide, 1.5%, 50° C., 1 hr
X—xylanase treatment, pH 5, 7 or 9, 60° C., 1 hr Kappa number is a measure of the amount of lignin in wood pulp. It is defined as the number of milliliters of 0.02M potassium permanganate solution which would be consumed by 1 gram of moisture-free pulp under AS 1301, APPITA P201 m-86, specified conditions.

It is evident from these results that bleaching in the presence of xylanase results in improved characteristics of brightness and kappa number, with yields comparable to that of the control. It is further evident that the xylanase gives optimal improvements in the alkaline pH range 7 to 9.

EXAMPLE 11

Use of B230 as a Bleaching Aid—Further Example

Figure 5:
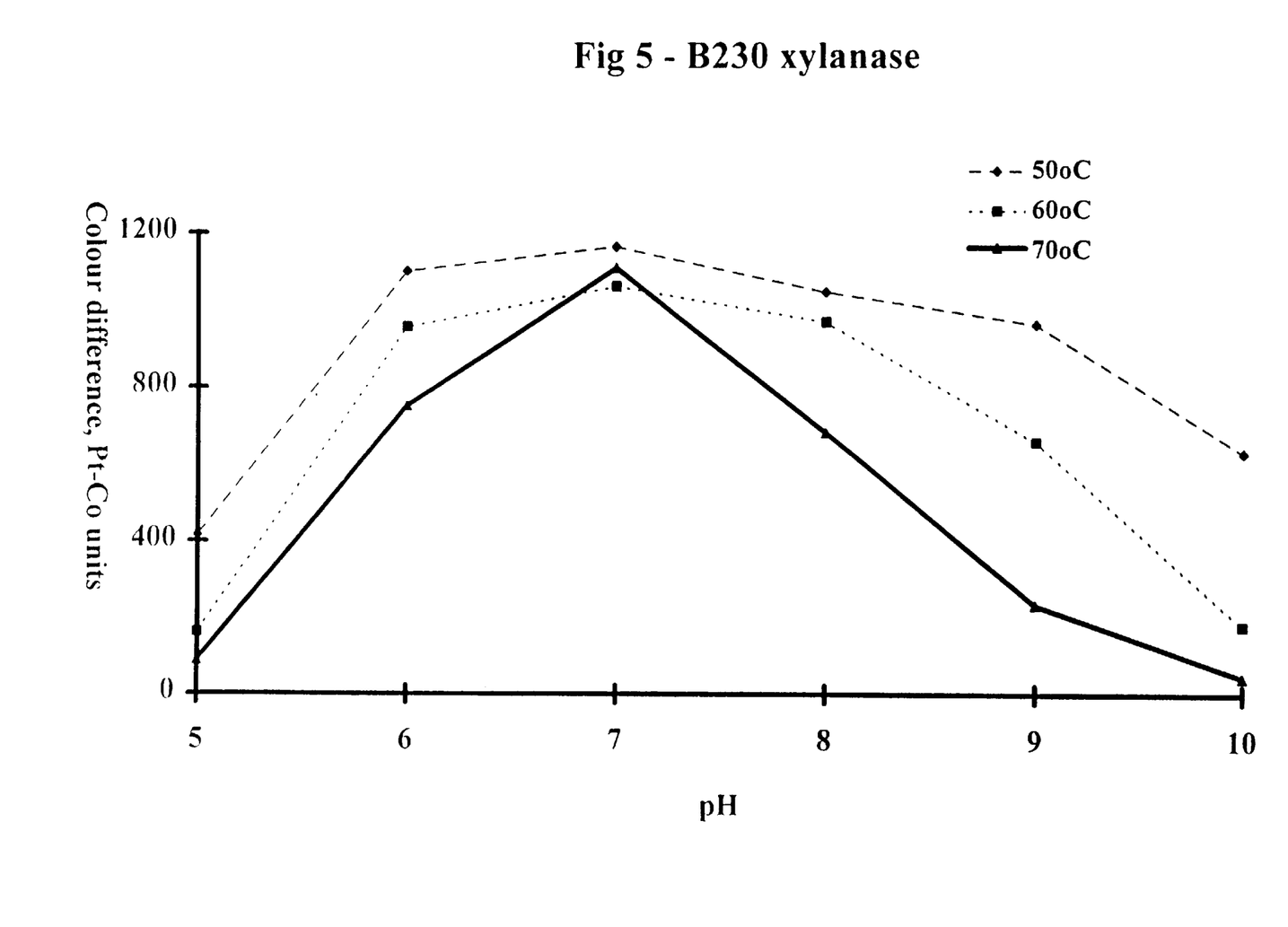
FIG. 5 illustrates the colour units release by xylanase from bacterium B230 at a range of pH and temperatures.

The crude xylanase system (167 nkat/g of pulp) was mixed with unbleached kraft pulp (35 g oven dried basis) at 8% consistency and adjusted to pH 5, 6, 7, 8, 9 or 10 with appropriate buffer. The mixture was incubated for 1 hr at either 50, 60 or 70° C. After the set time, the pulp was filtered to obtain a filtrate sample. The filtrate sample was briefly centrifuged and the absorbance at 456 nm was measured in a spectrometer. Absorbance units were converted to Pt-Co colour units from a standard graph where 500 colour units was obtained by dissolving $K_2PtCl_6$ (1.246 g), $CoCl_2.6H_2O$ (1.00 g) and HCl (100 mL, 12M) in 1L of water. The colour units released from the pulp by the xylanase is a measure of the final bleach chemical savings. The optimal effective pH was found to be pH 7, independent of temperatures between 50 and 70° C. (see FIG. 5).

EXAMPLE 12

Our earlier International Patent Application PCT/AU95/00202 describes a xylanase-producing bacterium designated B698, which was isolated from wood compost, and which was deposited under the Budapest Treaty in the Australian Government Analytical Laboratories as Accession No. 94/7647.

The temperature profile, pH profile, thermal stability at 60° C. and 65° C. at different pH values, and bleach boosting activity of xylanases for B230 and B698 were compared, using the methods described above, and the results are summarized in Tables 5 to 9.

TABLE 5

Xylanase pH Profile
Birchwood xylan, 50° C.

| | Relative Xylanase Activity (%) | |
|---|---|---|
| pH | B698 | B230 |
| 4 | 15 | 24 |
| 5 | 83 | 87 |
| 6 | 100 | 100 |
| 6.5 | 99 | Not determined |
| 7 | 77 | 72 |
| 8 | 69 | 76 |
| 9 | 37 | 32 |
| 10 | 11 | 11 |

TABLE 6

Xylanase Temperature Profile
Birchwood xylan, pH 6

| | Relative Xylanase Activity (%) | |
|---|---|---|
| Temperature | B698 | B230 |
| 40 | 65 | 45 |
| 50 | 85 | 63 |
| 60 | 100 | 100 |
| 65 | Not determined | 80 |
| 70 | 51 | 42 |
| 80 | 27 | 8 |

TABLE 7

Thermal Stability 60° C., 2 hrs

| | Relative Xylanase Activity (%) | |
|---|---|---|
| pH | B698 | B230 |
| 6 | 93 | 100 |
| 7 | 104 | 117 |
| 8 | 76 | 84 |
| 9 | 44 | 55 |

Note: At 60° C., pH 6, both B698 and B230 xylanases retained 90% of their activity after 22 hours.

TABLE 8

Thermal stability 65° C., 2 hrs

| | Relative Xylanase Activity (%) | |
|---|---|---|
| pH | B698 | B230 |
| 6 | 95 | 71 |
| 7 | 103 | 48 |
| 8 | 30 | 7 |
| 9 | 9 | 0 |

TABLE 9

Kraft Pulp Colour Difference
60° C., 1 hr

| | Colour Difference | |
|---|---|---|
| pH | B698 | B230 |
| 5 | 247 | 371 |
| 6 | 832 | 995 |
| 7 | 1084 | 1038 |
| 8 | 943 | 921 |
| 9 | 967 | 991 |
| 10 | 195 | 283 |

In general, the properties of the xylanases from the two organisms are very similar. However, 1. In solution, B698 xylanase retains more activity over a wider temperature range at pH 6. B698 xylanase is clearly more thermally stable at 65° C. over the pH range 6–9 than B230 xylanase.

2. In solution, at 50° C. there is no differentiation between the two enzymes over the pH range 4–10.

3. On kraft pulp, at 60° C., both B698 xylanase and B230 xylanase are effective bleach boosting agents over the pH range 6–9.

4. On kraft pulp, at 70° C., B230 xylanase is more effective than B698 as a bleach xylanase boosting agent. This is a significant advantage.

5. During fermentation, bacterium B230 expresses more xylanase than bacterium B698 (11,000 nkat/ml and 7,000 nkat/ml respectively.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

What is claimed is:

1. A bacterium or a derivative or mutant thereof, designated B230, as deposited in the Australian Government Analytical Laboratories under Accession No. N94/41262 which constitutively produces and/or extracellularly releases a xylanase which has an associated cellulase activity of less than 0.1% and wherein said xylanase is catalytically active at a pH of between about 6.5 and about 9.5 and at a temperature of between about 55° C. and 70° C.

2. A bacterium according to claim 1, wherein said xylanase is catalytically active at a pH of between about 7.5 and about 9.5 and at a temperature of between about 60° C. and 70° C.

3. A bacterium according to claim 1, wherein said xylanase is catalytically active at a pH of between about 7.5 and about 9.5 and at a temperature of about 65° C.

4. A bacterium according to claim 1, in which the xylanase is effective on both soluble and insoluble xylans.

5. An isolated xylanase which is produced by a bacterium as defined in claim 1.

* * * * *